United States Patent [19]
Marmar et al.
[11] Patent Number: 4,995,381
[45] Date of Patent: Feb. 26, 1991

[54] MALE THERAPEUTIC DEVICE

[75] Inventors: Joel L. Marmar, Cherry Hill, N.J.; Brian R. Henderson, Coopersburg, Pa.

[73] Assignee: Performance Plus, Inc., Berlin, N.J.

[21] Appl. No.: 415,823

[22] Filed: Oct. 2, 1989

[51] Int. Cl.[5] .......... A61F 5/41
[52] U.S. Cl. .......... 128/79
[58] Field of Search .......... 128/79; 606/140, 141

[56] References Cited

U.S. PATENT DOCUMENTS 3,759,253 9/1973 Cray .......... 128/79
4,539,980 9/1985 Chaney .......... 606/140
4,856,498 8/1989 Osbon .......... 128/79

FOREIGN PATENT DOCUMENTS 3606126 8/1987 Fed. Rep. of Germany .......... 128/79

*Primary Examiner*—Cary E. Stone
*Attorney, Agent, or Firm*—Norman E. Lehrer; Franklyn Schoenberg

[57] ABSTRACT

A therapeutic device is provided for assisting in the maintenance of an erection in a male penis which is a continuous ring prepared from a solid elastomeric material which is very soft, highly extensible and exhibits a very low modulus, the ring having a circular inner diameter and circular cross-section which is of a size adaptable to be readily placed about and snugly engage the base end of a penis with sufficient radial compressive force applied to the penis to restrict outward veinal flow of blood from the penis without complete occlusion of arterial blood flow.

10 Claims, 1 Drawing Sheet

10
18
2
2
16
12

10
18
2
2
16
12

10
16
18
14

MALE THERAPEUTIC DEVICE

FIELD OF THE INVENTION

The present invention relates to improved therapeutic devices for assisting males to effect or enhance an erection of the penis.

BACKGROUND OF THE INVENTION

Achievement of an erection is a natural process experienced by all men. In recent years considerable research has been performed on the erectile process. These include studies on the anatomy of the penis, the physical events associated with an erection, and new diagnostic tests.

The penis is composed of three cylinders. On the under side, there is a cylinder called the corpus spongiosum which contains the urethra and permits the flow of urine and ejaculate. Although this cylinder becomes distended during an erection, it does not become rigid. The remainder of the penis consists of two larger cylinders called corpora cavernosa. These are paired structures which occupy a majority of the space of the penis. During an erection, these cylinders fill with blood to produce firmness and rigidity. Each corpora is surrounded by a thick fibrous covering called the tunica albuginea. This covering has limited elasticity and distensibility. When the penis fills with blood and the corpora reach full size, the tunica albuginea will stretch to its limit and the penis becomes rigid.

Within the corpora, there are smooth muscle fibers, arteries, nerves and veins. These structures interact to produce an erection and 4 physical events occur as follows:

1. A stimulus (touch, feel, etc.) must be transmitted through the nerve endings within the penis to release a chemical known as a neurotransmitter.

2. This chemical in turn produces a dilation of the central artery of the corpora leading to an increase in arterial blood within the corpora.

3. The smooth muscle strands within the corpora relax to enable complete filling.

4. As the corpora distend and reach the elastic limit of its outer covering (tunica albuginea), the penile veins are compressed which limit the outflow of blood from the penis during erection.

X-rays of the penis known as cavernosography have demonstrated that approximately 60-80% of impotent men have "venous leakage." Another 10% of potent men also have minimal "venous leakage." In these men, the venous system does not compress during maximum filling which permits excessive drainage of blood from the penis leading to a premature and undesirable softening or detumescence. Heretofore, various types of ring appliances or devices such as, for example, disclosed in U.S Pat. Nos. 3,455,301, 3,461,863, 3,636,948, and 4,539,980 have been proposed which encircle the penis to prevent failing erections by restricting the return veinal flow. These prior art ring-like devices have been known as "cock rings."

Research on the erectile process has demonstrated that while the constrictor rings used in the past may be beneficial and reasonably effective for men with "venous leakage," they may not be safe because of possible penile strangulation, i.e., complete compromise to arterial blood flow. In U.S. Pat. Nos. 4,203,432 and 4,723,538, penile constriction ring devices for the treatment and alleviation of impotence in males are described which include some provision for adjusting the degree of constriction and/or for removing all constriction after a period of time. Such devices, however, are somewhat complex in construction and require significant manipulation by the user to be reasonably effective for their intended purpose.

SUMMARY OF THE INVENTION

It is an object of the present invention to provide a therapeutic device which is effective for maintenance of a male penile erection attained by natural or other means among men with "venous leakage" from the penis by restricting venous outflow from the penis for a period of time without complete occlusion of arterial blood flow and possible damage to the organ.

It is another object of the present invention to provide a therapeutic device which is readily put in place on the penis by a male user either before or during the attaining of an erection of the penis for assisting in maintaining the erection by restricting "venous leakage" and which, without conscious action by the user, will avoid complete occlusion of arterial blood flow and possible damage to the organ due to extended use of such device or additional enlargement of the organ.

It is a still further object of the present invention to provide a therapeutic device suitable for use by a male as a penile constrictor ring which can be readily put in place and removed by the user for assisting in maintaining a penile erection when natural processes have provided one and may also be useful in attaining and maintaining an erection where the natural process involved is not effective.

Yet another object of the invention is to provide a continuous ring of soft, highly extensible elastomeric material of a size that may be used as a therapeutic device for male penile organs of different diameters and can be readily put in place before or during the attaining of a penile erection by virtue of which it restricts "venous leakage" therefrom and serves as an aid for maintaining the penile erection without complete occlusion of arterial blood flow and possible damage to the organ.

In accordance with the present invention there is provided a therapeutic device for assisting in the maintenance of erection in the male penis comprising a continuous ring of elastic material having a substantially circular inner diameter and a circular cross-section adaptable to be placed about and snugly engage the base of a penis with sufficient radial compressive force applied thereto during a penile erection to restrict outward veinal flow of blood from the penis, said elastic material consisting essentially of a solid elastomeric material having a durometer (Shore A) hardness of between about 7 and 28, a tensile strength of at least about 300 psi, an elongation of at least about 600% and a tensile modulus at 100% elongation of less than about 50 psi, at 300% elongation of less than about 100 psi and at 600% elongation of less than about 200 psi.

The basic form of the erection assisting therapeutic device of the invention is an elastic constrictor ring of very soft but solid elastomeric material which is very extensible and has a relatively slow spring-back or recovery rate by virtue of which the ring can be radially stretched outwardly to enlarge the opening therein sufficiently for it to be readily put in place at the base of the penis before an erection has been attained or even after the erection thereof has been effected. The constrictor ring is of a size (e.g. ID about 1.5 cm, cross-sectional area about 1.0 sq.cm.) which will snugly fit about the base of a penis with a variety of diameters, and when in place, will provide sufficient radial compressive force to constrict the penile vein of an enlarged penis in erection and limit venous return of blood to assist in maintaining the erection.

Surprisingly and unexpectedly, the therapeutic device or constrictor ring of the invention provides veinal constriction sufficient to limit the outflow of blood from the penis during erection without complete occlusion of arterial blood flow, thus avoiding possible damage to the organ. Moreover, it has been found that the constrictor ring, when in place about the base of a penis, will readily expand in the event of further enlargement of the penis without penile strangulation and, more importantly, that after being in a stretched condition for a period of time, e.g. about 30 minutes, the elastomeric material will relax without conscious action of the user and the radial compressive forces imposed thereby will be reduced avoiding risk of potential penile strangulation or discomfort to the user. Further, the device of the invention may be effectively re-used after having been removed and stored for a short period of time in an unstressed condition.

Other objects and advantages of the present invention will become apparent from the detailed description thereof taken in conjunction with the drawing.

BRIEF DESCRIPTION OF THE DRAWINGS

For the purpose of illustrating the invention, there is shown in the accompanying drawing one form which is presently preferred; it being understood that the invention is not intended to be limited to the precise arrangements and instrumentalities shown.

DETAILED DESCRIPTION OF THE INVENTION

Figure 1:
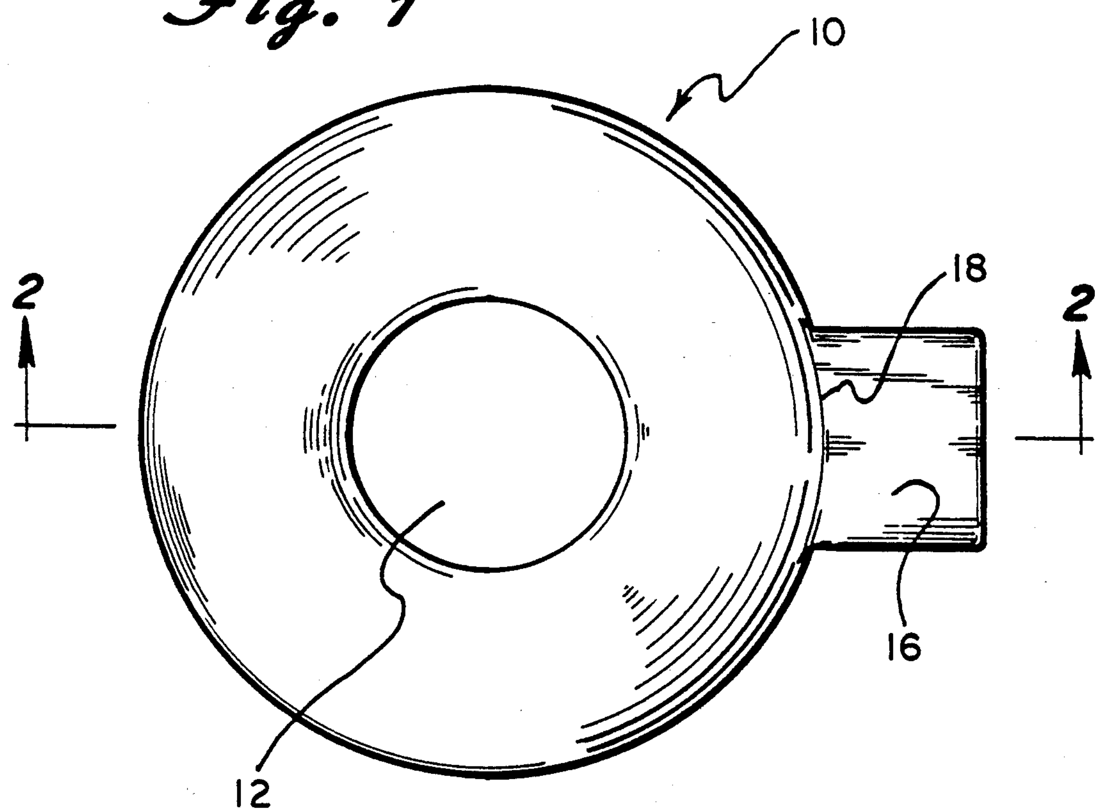
FIG. 1 is a plan view of a therapeutic device (constrictor ring) in accordance with the invention.
Figure 2:
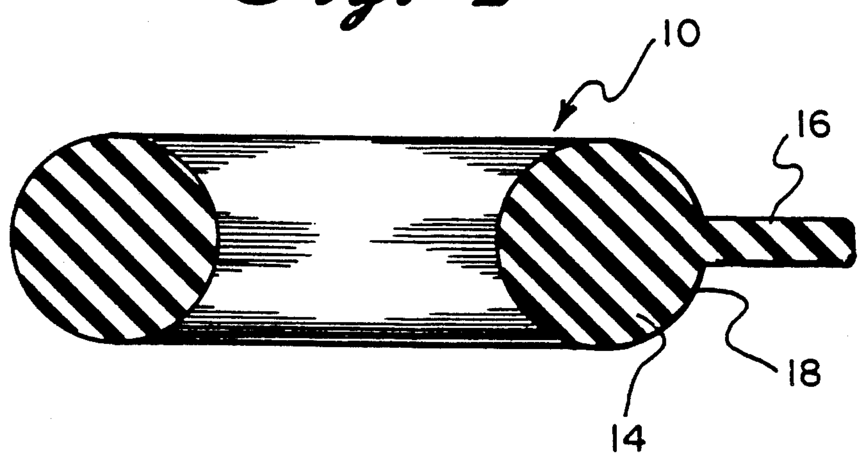
FIG. 2 is an enlarged sectional view taken along line 2—2 of FIG. 1.

Referring now to the drawing, where like reference numerals identify like parts, there is illustrated in FIGS. 1 and 2 a therapeutic device in accordance with the invention for assisting males to maintain an erection of the penis which comprises a continuous ring of very soft, highly extensible elastic material shown generally as 10 which has a substantially circular inner diameter or opening 12 and a circular cross-section 14. A grasping tab 16 extends laterally from the outer periphery 18 of the ring 10 to assist a user in expanding and positioning the ring but such member is not essential to operation of the device and may be eliminated, if desired.

The continuous ring 10 is molded from an elastomeric material, which when cured, is a highly extensible, very soft solid that exhibits a very low modulus and relatively slow spring-back or recovery rate. Suitable elastomeric materials must have a durometer (Shore A) hardness of from about 7 to about 28, preferably 10 to 25, a tensile strength of at least about 300 psi, an elongation of at least about 600% and a very low modulus, e.g. less than about 50 psi at 100% elongation, less than about 100psi at 300% elongation and less than about 200psi at 600% elongation. In general, while a variety of natural or synthetic elastomers including butyl rubber, polyurethane rubber, ethylene/propylene copolymers, polyisobutylene, chloroprene polymers, polybutadiene, polyisoprene, natural rubber and the like may be used to meet these requirements, elastomeric materials which conform to F.D.A. regulations for said therapeutic applications such as polysiloxane elastomers are preferred, and methyl vinyl polysiloxane elastomeric polymers are especially suitable. The ring 10 may be fabricated using conventional compression, transfer or injection molding and curing procedures, including if needed, post curing.

The constrictor ring 10 should have an appropriate internal diameter or opening 12 and cross-sectional size 14 to provide the needed assistance for maintaining a penile erection, and preferably, to adapt properly to various males. The ring 10 must have an appropriate opening 12 to snugly fit about the base of a penis when positioned in advance of expected use or after attaining an erection, and a cross-section 14 to provide sufficient radial compressive force to constrict the penile veins of an enlarged penis in erection and limit the out-flow of blood through the veins without complete occlusion of arterial blood flow.

Surprisingly and unexpectedly, it has been found that a ring 10 in accordance with the invention as herein described may generally be suitable for use by males with a large variety of penile diameters, although more than one size ring could be provided where needed. By way of example, a ring in accordance with the invention having an internal diameter or opening 12 of about 1.5 cm and a cross-sectional area 14 of about 1 sq.cm. was suitable for use by a large group of males (over 100) with varying penile diameters during clinical trials. Moreover, it was found that such rings retained considerable elastic potential to avoid strangulation of the organ in the event of further enlargement thereof, that the compressive forces radially imposed thereby were reduced after a period of continuous expansion (30–60 minutes) without conscious effort of the user, and that even though the spring-back or recovery rate of the ring was relatively slow, its original configuration and effectiveness was substantially restored after a short period of unstressed storage.

To use the device 10, two or three fingers on each hand are inserted in the opening 12 in the ring and the ring is stretched for placement about the penis, preferably being slipped thereover to its base adjacent the users body before the fingers are removed. The ring 10 contracts sufficiently to snugly fit about the base of the penis without occlusion of arterial blood flow into the penis or other discomfort. Placement of the ring will restrict veinal out-flow from the penis during its enlargement and after an erection has been attained, thus assisting the user in maintaining the erection by virtue of limiting "venous leakage." The ring may be easily stretched to remove the same when desired, although after a short period of time (about 30–60 minutes) the ring material will gradually relax with the compressive forces imposed thereby being reduced without conscious action by the user, thus avoiding penis strangulation or discomfort if the ring is not promptly removed.

The invention as described above is further illustrated by the following examples, which are intended to be illustrative of and not limitative in any way of the invention.

EXAMPLE 1

A quantity of rings such as illustrated in FIGS. 1 and 2 were prepared from two methyl vinyl polysiloxane elastomeric polymer compositions (Composition A and Composition B) using conventional molding and curing procedures, and then post cured 4 hours at 400° F. The average properties of the cured elastomer are summarized below:

| | Comp. A | Comp. B |
|---|---|---|
| Durometer Hardness (A) | 20 | 10 |
| Tensile (psi) | 520 | 320 |
| Elongation (%) | 900 | 900 |
| Modulus (psi) | | |
| 300% Elong. | 66 | 50 |
| 400% | 97 | 69 |
| 600% | 196 | 140 |
| 800% | 360 | 220 |

Rings having a diameter opening of 1.5 cm and a cross-sectional area of 1 sq.cm. were used in clinical trials in which over 100 patients participated, including men with vascular insufficiency. The rings were put in place by the individual patients without difficulty or discomfort to the user. Blood flow studies by pneumoplethysmography fail to demonstrate any changes from baseline flow after using rings made from Compositions A and B. Furthermore, no traumatic side effects were reported. During the trials, one patient wore the ring continuously for 12 hours without pain or other complications and at least 2 patients fell asleep with the ring in place, after which a healthy circulation within the penis was observed when the patient awoke. The rings were removable after each use by the individual patients without difficulty

EXAMPLE 2

A quantity of rings such as illustrated in FIGS. 1 and 2 were prepared from another methyl vinyl polysiloxane elastomer composition (Composition C) using conventional molding and curing procedures. The properties of the cured elastomer are summarized below:

| | Comp C |
|---|---|
| Durometer Hardness (A) | 25 |
| Tensile Strength (psi) | 720 |
| Elongation (%) | 900 |
| Modulus (psi) | |
| 300% E | .92 |
| 400% | 125 |
| 600% | 255 |
| 800% | 600 |

During a series of clinical studies with over 100 patients, rings having an ID of 1.5 cm and a cross-sectional area of 1 sq.cm. made from Composition C, which exhibit a significantly higher modulus than Composition A and Composition B, were found to be too restrictive of blood flow and uncomfortable to use for an extended period of time. Thus, rings made from Composition C were not considered acceptable.

While the invention has been described and exemplified in detail, various modifications and improvements should become apparent to those skilled in the art without departing from the spirit and scope of the invention.

What is claimed is:

1. A therapeutic device for assisting in the maintenance of an erection in the male penis comprising a continuous ring of elastic material having a substantially circular inner diameter and a circular cross-section adaptable to be placed about and snugly engage the base end of a penis with sufficient radial compressive force applied thereto during a penile erection to restrict outward venial flow of blood from the penis without complete occlusion of arterial blood flow, said elastic material consisting essentially of a very soft solid elastomeric material having a durometer hardness (Shore A) of between about 7 and 28 which is highly extensible, exhibits a very low modulus and will relax sufficiently after a period of use without conscious effort of a user to reduce the radial compressive force imposed thereby.

2. The therapeutic device according to claim 1, wherein said elastomeric material has a tensile strength of at least about 300 psi an elongation of at least about 600% and a tensile modulus at 100% elongation of less than about 50 psi, at 300% elongation of less than about 100 psi.

3. The therapeutic device according to claim 1, wherein said elastomeric material has a tensile strength of at least about 300 psi, an elongation of at least about 600% and a tensile modulus at 400% elongation of less than about 100 psi and at 600% elongation of less than about 200 psi.

4. The therapeutic device according to claim 3, wherein said elastomeric material is a methyl vinyl polysiloxane.

5. The therapeutic device according to claim 4, wherein the inner diameter of said ring is about 1.5 cm and the cross-sectional area thereof is about 1 sq.cm.

6. The therapeutic device according to claim 1, wherein said elastomeric material conforms to F.D.A. regulations for therapeutic applications.

7. The therapeutic device according to claim 1, wherein said elastomeric material is a methyl vinyl polysiloxane.

8. A therapeutic device for assisting in the maintenance of an erection in a male penis comprising a continuous ring of elastic material having a substantially circular inner diameter of about 1.5 cm. and a circular cross-section of about 1 sq.cm. in area which is adaptable to be placed about and snugly engage the base end of a penis with sufficient radial compressive force applied thereto during a penile erection to restrict outward veinal flow of blood from the penis, said elastic material consisting essentially of a cured methyl vinyl polysiloxane having a durometer hardness (Shore A) of between about 7 and 28, a tensile strength of at least about 300 psi, an elongation of at least about 600%, and a tensile modulus at 100% elongation of less than about 50psi, at 300 elongation of less than about 100 psi, and at 600% elongation of less than about 200 psi.

9. The therapeutic device according to claim 8, wherein said ring of elastic material applies a sufficient radial compressive force to restrict outward veinal flow of blood without complete occlusion of arterial blood flow, and said ring will relax sufficiently after a period of use without conscious effort of a user to reduce the radial compressive force and the restriction of veinal imposed thereby.

10. The therapeutic device according to claim 8, wherein said elastic material has a durometer hardness (Shore A) up to 25.

* * * * *